Figure 1:
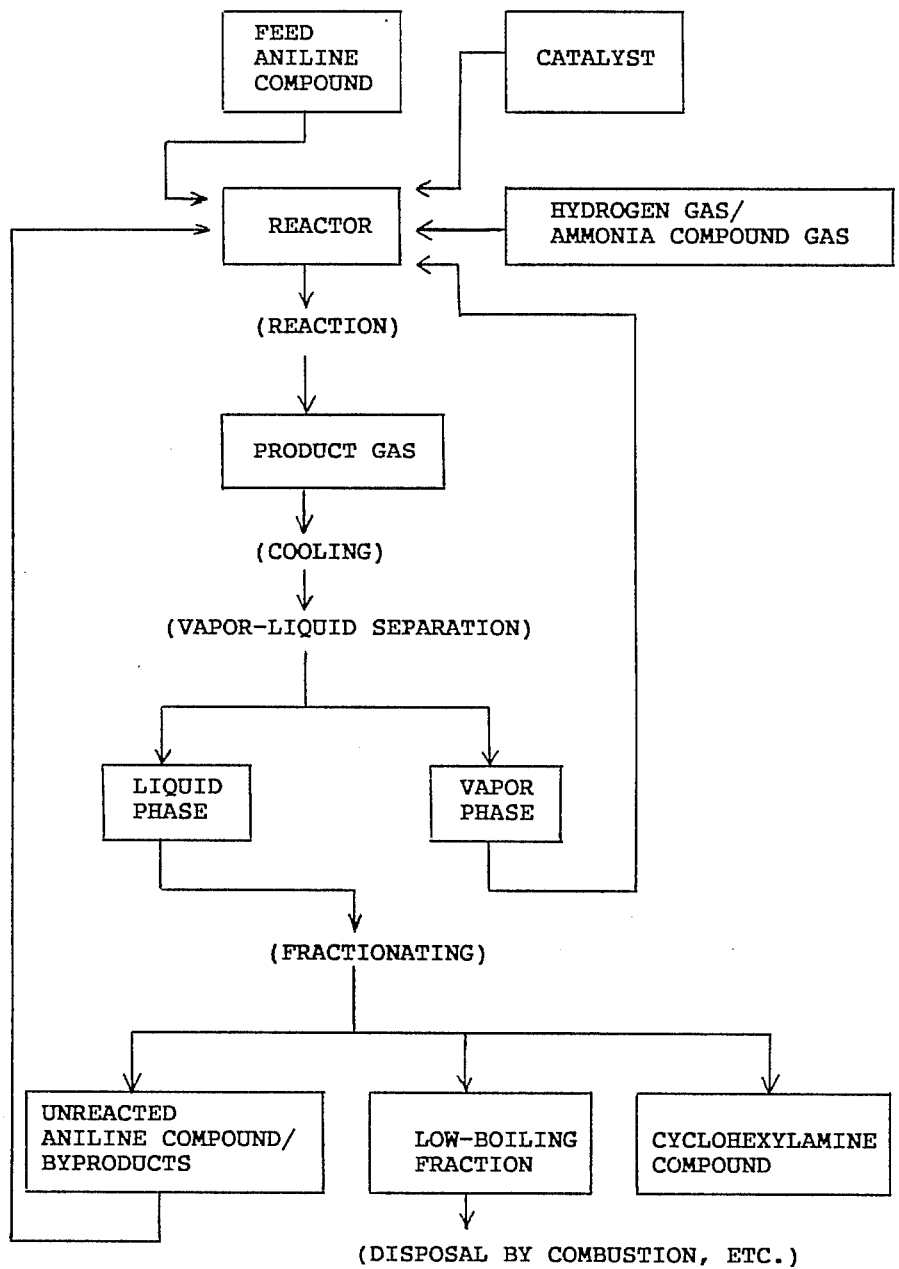

United States Patent [19]

Kiyuma et al.

[11] Patent Number: 4,914,239

[45] Date of Patent: Apr. 3, 1990

[54] METHOD FOR PRODUCTION OF CYCLOHEXYLAMINES

[75] Inventors: Tatsuo Kiyuma, Uji; Isao Naramoto, Tokushima, both of Japan

[73] Assignee: New Japan Chemical Co., Ltd., Kyoto, Japan

[21] Appl. No.: 178,722

[22] Filed: Apr. 6, 1988

[30] Foreign Application Priority Data

Jun. 24, 1987 [JP] Japan .................................. 62-157256
Feb. 17, 1988 [JP] Japan .................................. 63-34561

[51] Int. Cl.$^4$ .............................................. C07C 87/36
[52] U.S. Cl. ...................................................... 564/450
[58] Field of Search .......................................... 564/450

[56] References Cited

U.S. PATENT DOCUMENTS 3,565,921  2/1971  Gobron et al. ................... 260/347.8

FOREIGN PATENT DOCUMENTS

| 43-3180 | 2/1943 | Japan . |
|---|---|---|
| 45-19897 | 7/1970 | Japan . |
| 45-19898 | 7/1970 | Japan . |
| 45-28368 | 9/1970 | Japan . |
| 51-41627 | 11/1976 | Japan . |
| 55-51042 | 4/1980 | Japan . |
| 59-196843 | 11/1984 | Japan . |
| 60-239444 | 11/1985 | Japan . |
| 506928 | 6/1939 | United Kingdom . |
| 836951 | 6/1960 | United Kingdom . |
| 989322 | 4/1965 | United Kingdom . |

*Primary Examiner*—Richard L. Raymond
*Assistant Examiner*—Peter G. O'Sullivan
*Attorney, Agent, or Firm*—Armstrong, Nikaido, Marmelstein, Kubovcik & Murray

[57] ABSTRACT

Disclosed is a method for continuous production of a cyclohexylamine compound by liquid phase hydrogenation of an aniline compound selected from aniline, nuclearly lower alkyl-substituted aniline, N-(lower alkyl)aniline and N,N-di(lower alkyl)aniline with hydrogen gas in the presence of a nickel catalyst, which comprises continuously feeding an aniline compound, continuously hydrogenating the aniline compound in the absence of a solvent and in the presence of an ammonia compound at a reaction pressure of about 2 to 10 kg/cm$^2$ and at about 210° to 240° C., continuously withdrawing a product gas containing product cyclohexylamine compound, unreacted aniline compound, byproducts, hydrogen and ammonia compound from the reaction system, separating the hydrogen and ammonia compound from the product gas, separating the unreacted aniline compound and byproducts from the cyclohexylamine compound and recycling the unreacted aniline compound and byproducts to the reaction system continuously together with starting material feed aniline compound.

10 Claims, 1 Drawing Sheet

METHOD FOR PRODUCTION OF CYCLOHEXYLAMINES

The present invention relates to a method of producing cyclohexylamines. More particularly, the invention relates to a method of producing a cyclohexylamine compound from an aniline compound which comprises performing nuclear hydrogenation of the aniline compound with the aid of a nickel catalyst in the presence of ammonia or an amine.

Cyclohexylamine is a useful intermediate for the production of rubber vulcanizing additives, metal corrosion inhibitors, dyestuffs, agrochemicals, drugs and so on. Among the known production processes for cyclohexylamine is the process in which cyclohexylamine is produced from cyclohexanone, cyclohexanol or phenol in the presence of ammonia and hydrogen (Japanese Unexamined Patent Publications (Kokai) No. 60-239444 and No. 55-51042, Japanese Examined Patent Publications No. 45-19898, No. 51-41627 and No. 45-19897, etc.).

An alternative known method comprises nuclear hydrogenation of aniline. Generally, the reaction giving cyclohexylamine by the hydrogenation of aniline involves the following side or secondary reactions.

(1) Formation of dicyclohexylamine due to deaminative dimerization of cyclohexylamine (2) Formation of N-cyclohexylaniline due to deaminative dimerization of cyclohexylamine and aniline (3) Formation of cyclohexanol due to hydrolysis of cyclohexylamine or hydration of cyclohexene (4) Formation of cyclohexene due to deamination of cyclohexylamine and formation of cyclohexane as a hydrogenation product thereof (5) Formation of a trimer or polymer (hereinafter referred to collectively as polymer) among cyclohexylamine, dicyclohexylamine and aniline.

Therefore, it is essential to inhibit or suppress these side or secondary reactions and to efficiently separate the byproducts from the desired product, i.e., cyclohexylamine.

Production of cyclohexylamine by nuclear hydrogenation of aniline under the conventional operating conditions (for example, using a nickel catalyst at a hydrogen pressure of 100 kg/cm$^2$ and a reaction temperature of 150°–200° C.) results in a premature termination of hydrogen absorption to give cyclohexylamine containing more than 50% of unreacted aniline. To avoid this problem, various techniques such as the use of a modified nickel catalyst or the use of a palladium or other catalyst has been suggested as stated below.

(1) Japanese Examined Patent Publication No. 43-3180 discloses a process in which cyclohexylamine is produced by liquid-phase hydrogenation of aniline. In this process, a Raney cobalt catalyst and, as cocatalysts, calcium oxide and sodium carbonate are employed This production process yields 96.2% of cyclohexylamine, 2.1% of dicyclohexylamine, 0.5% of cyclohexane and 1.2% of unreacted aniline However, the process has the disadvantages that a high reaction pressure of 30 to 100 kg/cm$^2$, preferably 50 to 70 kg/cm$^2$, is required, that the side reactions cannot be fully controlled even by the addition of calcium oxide, and that the preparation of the catalyst involves an additional step of incorporating calcium oxide and sodium carbonate.

(2) Japanese Examined Patent Publication No. 45-28368 discloses a process for producing cyclohexylamine from aniline in vapor phase which is characterized by adding a basic alkali metal compound to the nickel catalyst. The disadvantages of this technique are that because it involves a vapor phase reaction, the molecular density per unit volume is low and, hence, the output per unit time is also small and that the formation of byproducts cannot be fully controlled even by the addition of the basic alkali metal. Moreover, the catalyst preparation requires strict control for assuring a constant alkali metal level in the catalyst.

(3) Japanese Unexamined Patent Publication (Kokai) No. 59-196843 discloses a production process for cyclohexylamine in which aniline or a nuclearly substituted aniline is hydrogenated with the aid of a palladium catalyst at room temperature to 160° C. The disadvantages of this method are that the expensive palladium catalyst must be used and that as the reaction time is as long as 12 hours, the productivity of the process cannot be said to be high.

(4) U.S. Pat. No. 3,565,921 discloses a process in which using a dispersion of the nickel catalyst in an inert solvent such as 2-ethylhexyl-2-ethylhexanoate, the nuclear hydrogenation of aniline is continuously carried out at about 180° C. and under atmospheric pressure, giving cyclohexylamine and in which the conversion of aniline is 86.5%. Whereas conversion of aniline is approximately 50 percent in the conventional liquid-phase batch processes, the continuous liquid-phase reaction according to the above United States patent is excellent from the standpoint of yield. However, the method is disadvantageous in that the deamination of aniline or cyclohexylamine is not sufficiently suppressed and that the use of said inert solvent inevitably causes an increased cost of production. Moreover, the inert solvent must have a boiling point higher than the nuclear hydrogenation temperature by at least about 50° C. and if the reaction temperature is increased to enhance the reaction rate, the choice of a solvent will be restricted.

As will be apparent from the above brief notes on the prior art, the conventional techniques for the production of cyclohexylamine by nuclear hydrogenation of aniline are not fully satisfactory but each has much room for improvement.

It is an object of the present invention to provide a method for producing a cyclohexylamine compound with high productivity using a catalyst which is inexpensive and easy to handle.

It is a further object of the invention to provide a method for producing a cyclohexylamine compound in high yield under comparatively low pressure conditions with a minimum of formation of byproducts.

Thus, the present invention provides a method for continuous production of a cyclohexylamine compound by liquid phase hydrogenation of an aniline compound selected from aniline, nuclearly lower alkyl-substituted aniline, N-(lower alkyl)aniline and N,N-di(lower alkyl)aniline with hydrogen gas in the presence of a nickel catalyst, which comprises continuously feeding an aniline compound, continuously hydrogenating the aniline compound in the absence of a solvent and in the presence of an ammonia compound at a reaction pressure of about 2 to 10 kg/cm$^2$ and at about 210° to 240° C., continuously withdrawing a product gas containing product cyclohexylamine compound, unreacted aniline compound, byproducts, hydrogen and ammonia compound from the reaction system, separating the hydrogen and ammonia compound from the product gas, separating the unreacted aniline compound and byproducts from the cyclohexylamine compound and recycling the unreacted aniline compound and byproducts to the reaction system continuously together with starting material feed aniline compound, wherein the ammonia compound is ammonia when the aniline compound is aniline or nuclearly lower alkyl-substituted aniline; the ammonia compound is mono(lower alkyl)amine when the aniline compound is N-(lower alkyl)aniline; and the ammonia compound is di(lower alkyl)amine when the aniline compound is N,N-di(lower alkyl)aniline.

The present inventors explored the factors responsible for the recovery of unreacted aniline and for the formation of dicyclohexylamine and other byproducts in the conventional process for nuclear hydrogenation of aniline. Consequently, we found that the higher basicity of the product cyclohexylamine than that of aniline causes an intense adsorption of cyclohexylamine on the nickel catalyst to thereby block the adsorption of aniline on the catalyst and hence interrupt the reaction and that the prolonged retention of cyclohexylamine on the catalyst causes various secondary reactions.

This implies that the product cyclohexylamine should preferably be removed from the reaction system as soon as it is formed. However, since the conventional liquid phase hydrogenation reaction using a nickel catalyst generally requires a reaction temperature of about 150° to 200° C. and a hydrogen pressure of not less than 50 kg/cm$^2$, it is difficult to find conditions such that the product cyclohexylamine may be distilled out from the reaction system, with the unreacted aniline substantially retained within the reaction system.

In the method of U.S. Pat. No. 3,565,921 which is characterized by hydrogenation at atmospheric pressure, the reaction is conducted at a temperature higher than the boiling point of aniline and that of cyclohexylamine, and these conditions make it imperative to employ an inert solvent capable of dissolving aniline and cyclohexylamine, such as 2-ethylhexyl-2-ethylhexanoate.

Under the circumstances, the present inventors conducted a detailed analysis of the vapor pressures of cyclohexylamine compound, aniline compound and byproducts as well as the temperature condition at which the activity of the nickel catalyst may be suitably maintained and the causes and conditions giving rise to dicyclohexylamine and other byproducts. The present invention has been developed on the basis of the result of the analysis.

Thus, the objects of the invention are accomplished by conducting the hydrogenation reaction under a low pressure conducive to the accelerated evaporation or distillation of product cyclohexylamine compound and at a higher hydrogenation temperature than usual.

The present invention provides the following outstanding advantages.

(1) First, an inexpensive nickel catalyst which is easy to handle or prepare can be utilized.

(2) Secondly, the higher reaction temperature leads to a higher reaction rate and the lower reaction pressure does not require the use of a reactor of high pressure resistance.

(3) Thirdly, as the unreacted aniline compound and byproducts separated from cyclohexylamine compound, for example, by distillation are continuously returned to the reaction system, the product cyclohexylamine compound can be obtained in an unusually high yield of more than about 99% based on the feed aniline compound.

(4) In the fourth place, the presence of the ammonia compound in the reaction system inhibits secondary reactions. Thus, when ammonia compound is present in the reaction system, the deamination reaction of aniline compound and cyclohexylamine compound is suppressed and the byproducts dicyclohexylamine and others are converted to cyclohexylamine compound. There is no prior art technology for liquid phase nuclear hydrogenation with a nickel catalyst in the presence of said ammonia compound.

(5) In the fifth place, since the charge of the starting material aniline compound, hydrogen, ammonia compound, unreacted aniline compound and byproducts is continuously carried out, the productivity of the operation is remarkably enhanced.

The production method according to the invention is described below with reference to the accompanying drawing.

FIG. 1 is a flow chart showing an embodiment of the production method according to the invention.

The starting material in this invention is an aniline compound. The aniline compound includes not only aniline but also aniline derivatives such as nuclearly lower alkyl-substituted aniline, N-(lower alkyl)aniline, N,N-di(lower alkyl)aniline, and so on, and these compounds are converted, in high yield, to a corresponding cyclohexylamine compound, i.e., to cyclohexylamine, nuclearly lower alkyl-substituted cyclohexylamine, N-lower alkyl-cyclohexylamine, and N,N-di(lower alkyl)-cyclohexylamine, respectively. As examples of the lower alkyl groups mentioned herein as substituents, there may be mentioned alkyl groups containing 1 to 2 carbon atoms, such as methyl and ethyl. The nuclearly lower alkyl-substituted aniline includes monomethyl- and dimethyl-substituted aniline and monoethyl-substituted aniline. Thus typical examples of the aniline compounds to be used in the invention include aniline, N-methylaniline, N-ethylaniline, N,N-dimethyl-aniline, N,N-diethylaniline, nuclearly monomethyl-substituted aniline, nuclearly monoethyl-substituted aniline and nuclearly dimethyl-substituted aniline.

When the aniline compound is aniline or nuclearly lower alkyl-substituted aniline, ammonia compound to be used as an inhibitor of side reactions should be ammonia. When the aniline compound is N-(lower alkyl)aniline, the ammonia compound should be a corresponding mono(lower alkyl)amine, and when the aniline compound is N,N-di(lower alkyl)aniline, the ammonia compound should be a corresponding di(lower alkyl)amine. For example, when the aniline compound is N-methylaniline, the ammonia compound should be methylamine, and when the aniline compound is N,N-diethylaniline, the ammonia compound should be diethylamine.

While aniline and ammonia are mainly referred to in the following description, the production method of the invention can be applied as well to the aniline derivatives and mono- or di(lower alkyl)amine mentioned above.

The catalyst to be used in the invention is preferably a stabilized nickel catalyst obtainable by supporting nickel on an appropriate support such as diatomaceous earth, alumina, silica or the like, and Raney nickel catalyst can also be employed. The stabilized nickel and Raney nickel catalysts can each be prepared in the conventional manner. The amount of nickel metal in the stabilized nickel catalyst may range from about 5 to 70 weight percent. The proportion of the catalyst is preferably in the range of about 5 to 40 weight percent based on the total weight of the liquid phase components of the reaction system.

In the practice of the invention, hydrogen for hydrogenation and ammonia compound as an inhibitor of side reactions are preferably used as a gaseous mixture such that the mol ratio of hydrogen to ammonia compound is preferably in the range of 5:0.5-3.

The reaction vessel for use in the practice of the invention may be any reactor that withstands a pressure of about 2 to 10 kg/cm$^2$ and a cylindrical reactor or column is preferred.

In accordance with the invention, the abovementioned reactor is first charged with the catalyst and starting material aniline. The concentration of the catalyst is virtually optional and can be selected from a broad range but it may generally be about 5 to 30 weight percent based on the aniline feed. The atmosphere in the reactor is purged with hydrogen gas and, then, said hydrogen-ammonia mixture gas is introduced from the bottom of the reactor in such a manner that it may flow through the body of starting material aniline at a suitable velocity, for example at a linear space velocity of about 2 to 20 cm/sec. The pressure in the reactor is increased to about 2 to 10 kg/cm$^2$ and at the same time the temperature is increased to about 190° C. by external heating, for example with steam. Thereupon, the hydrogenation reaction begins to proceed and the resulting heat of reaction further elevates the temperature of the reaction system to about 210° to 240° C.

Thereafter, the reaction pressure and temperature are maintained at the levels to be stated below by controlling the feeding rate of hydrogen-ammonia mixture gas, and the starting material aniline is also continuously supplied to the reactor for hydrogenation reaction, with the product cyclohexylamine being continuously distilled out.

The feeding rate of hydrogen-ammonia mixture gas is controlled at a linear space velocity of about 2 to 20 cm/second, preferably about 7 to 9 cm/second. If the feeding rate is less than the above range, the distillation or vaporization of cyclohexylamine is retarded to result in increased secondary reactions and a decreased reaction rate. Conversely if the feeding rate is higher than the above range, the unreacted aniline and byproducts tend to be more easily distilled out together with product cyclohexylamine so that the efficiency of fractional separation is lowered and the productivity of the operation decreased.

The reaction pressure is preferably controlled under about 2 to 10 kg/cm$^2$ and more desirably at about 6.5 to 7.5 kg/cm$^2$. The hydrogenation reaction is still feasible under a pressure of at least 1 kg/cm$^2$ but is retarded under a pressure below 2 kg/cm$^2$. Conversely, if the pressure exceeds about 10 kg/cm$^2$, the mol fraction of cyclohexylamine in the product gas is reduced so that a large amount of hydrogen gas must be circulated, thus detracting from the economics of production.

The reaction temperature is preferably about 210° to 240° C. If the temperature is below 210° C., the product cyclohexylamine will not be sufficiently distilled out and, moreover, the hydrogenation reaction is retarded. If the temperature exceeds the upper limit of about 240° C., the separation of unreacted aniline and dicyclohexylamine and other byproducts from the product cyclohexylamine will become difficult and, moreover, side reactions are promoted and the catalyst also tends to be degraded.

The reaction temperature can be almost automatically controlled in the above-mentioned range of about 210° to 240° C. as the feeding rate of hydrogen-ammonia gas is maintained within the above-mentioned range. Thus, introducing the hydrogen-ammonia gas into the reactor sets the reaction going, with evolution of the heat of reaction. At the same time, as the product cyclohexylamine and others are distilled out, the heat of reaction is consumed as the heat of vaporization. Though the heat of reaction is slightly greater than the heat of vaporization, the two are kept in substantial balance. If the reaction temperature exceeds about 240° C., the reaction system may be cooled by means of water-cooling pipe or other conventional cooling means to maintain the temperature within the range of about 210° to 240° C. Thus, the present invention has the advantage that the reaction temperature can be controlled by mere control of gas flow without resort to complicated temperature control.

The starting material aniline is generally fed continuously from the bottom of the reactor with advantage. The feeding rate of aniline is preferably the rate necessary for the maintenance of steady state of reaction, that is to say the rate which assures a constant distillation or evaporation of the product cyclohexylamine from the reaction system and a constant amount of liquid phase in the reaction system. Taking a reactor with a capacity of 10 m$^3$ as an example, feeding the starting fresh raw material aniline at a rate of 500 kg to 2 tons/hour under the above-mentioned temperature, pressure and hydrogen-ammonia gas flow conditions easily leads to a steady state of reaction.

Under the above conditions, cyclohexylamine produced is immediately distilled out or vaporizes as a product gas from the reaction system together with minor amounts of unreacted aniline and byproducts, and hydrogen and ammonia Since the distillation or vaporization of unreacted aniline and byproducts is not appreciable under the above conditions, the product cyclohexylamine can be separated from the other distillates with high efficiency. In addition, the desorption of cyclohexylamine from the catalyst is rapidly effected so that the formation of byproducts inclusive of polymer is suppressed, assuring a long catalyst life.

When aniline is the starting material, the byproducts distilled out together with cyclohexylamine under the above conditions are dicyclohexylamine, cyclohexene, cyclohexane, N-cyclohexylaniline and so on, and the composition of the product gas excepting hydrogen and ammonia is about 70-85% (weight %; the same applies hereinafter) of cyclohexylamine, about 3-7% of unreacted aniline, about 10-18% of dicyclohexylamine, about 1-3% of N-cyclohexylaniline, and less than about 1% of cyclohexene and cyclohexane.

When cooled, product gas is readily separated into a vapor phase consisting essentially of hydrogen and ammonia gases and a liquid phase consisting essentially of the product cyclohexylamine, unreacted aniline and byproducts. For this cooling operation, the ordinary condenser can be employed and the product gas is cooled to a temperature not exceeding about 60° C. under the above pressure conditions.

The separated vapor phase consisting essentially of hydrogen and ammonia gases can be recycled, either directly or after purification, into the hydrogenation reaction system as a part of the hydrogen-ammonia gas fed to the reactor, whereby the hydrogen-ammonia gas mixture can be effectively utilized.

On the other hand, the cyclohexylamine in the liquid phase can be isolated by fractionating distillation of the liquid phase. This fractionating purification can be effected in a column of at least about 10 trays under atmospheric pressure or reduced pressure, for example about 200 to 500 mmHg. In this connection, it is preferable to use two fractionating distillation columns so that a lower-boiling fraction mainly composed of cyclohexane and cyclohexene is separated in a first column and the product cyclohexylamine is separated from other substances such as unreacted aniline, dicyclohexylaniline and N-cyclohexylaniline in a second column. Of course, the above fractionating distillation can be effected using a single distillation column. In any event, it is easy for those skilled in the art to separate cyclohexylamine from unreacted aniline and byproducts by fractionating distillation and any known procedure for the like purpose can be utilized.

The unreacted aniline and byproducts (particularly the byproducts other than low-boiling substances such as cyclohexene and cyclohexane) can be recycled, in their entirety, to the reaction system for conversion to cyclohexylamine. Furthermore, the productivity of the operation can be enhanced by conducting the above steps continuously. Since the output of low-boiling fraction such as cyclohexane and cyclohexene is small, it may be disposed of by combustion or the like.

Referring to the procedure of recycling the unreacted aniline and byproducts to the reactor for rereaction, the proportion thereof in the reactor charge, relative to the fresh raw starting material aniline, can be selected from a broad range but generally the proportion is about 0.05 to 0.5 part by weight, preferably about 0.2 to 0.4 part by weight, per part by weight of the fresh feed aniline. If the proportion is less than this range, the unreacted aniline and byproducts will increase in a cushion tank or the like. If the proportion exceeds the above range, the charge amount of the starting material aniline is decreased and the product yield lowered.

After recycling of the unreacted aniline and byproducts to the reaction system for re-reaction, the reaction can still be continuously conducted in the same manner as described above at the same pressure and temperature using said hydrogen-ammonia gas feeding rate and, then, the separation of cyclohexylamine from the product gas and the recycling of unreacted aniline and byproducts can also be performed in the same manner as described above. The feeding of starting material aniline and of recycled unreacted aniline and byproducts is preferably performed at such a rate as to keep the amount of liquid phase in the reactor constant.

By such a continuous operation, the consumption of the catalyst can be reduced to 1 kg or less for the production of 1 ton of cyclohexylamine.

Furthermore, since the nuclear hydrogenation of aniline is so rapid under the conditions of the present invention that the retention time within the reactor is only about 5 to 120 minutes, thus contributing considerably to increased productivity.

In addition, all the byproducts that cannot be converted to cyclohexylamine by the above re-reaction are cyclohexene and cyclohexane, whose amount is no more than about 0.5 percent, and the polymer, the proportion of which is not more than 0.1 percent. Therefore, the yield of purified cyclohexylamine based on aniline feed is not less than about 99.4 percent.

Thus, the production method of the present invention provides for an efficient production of cyclohexylamine compound in high yield and purity and is, therefore, of high industrial value.

The following examples are further illustrative of the present invention and should by no means be construed as limiting the scope of the invention.

EXAMPLE 1

A reaction column with an internal diameter of 1 m and a capacity of 10 m$^3$ was charged with 150 kg of a stabilized nickel catalyst (SN-110, Sakai Chemical Co., Ltd., supported on diatomaceous earth) and 2 tons of aniline and the internal atmosphere was replaced with hydrogen gas. Then, while hydrogen-ammonia gas mixture (mol ratio 5:1) was continuously introduced from the bottom of the reaction column to maintain the internal pressure of 7 kg/cm$^2$ and a linear space velocity of 7 cm/second, the internal temperature was increased to 190° C.

The temperature was then automatically increased by the reaction heat of hydrogenation. With the feeding rate of hydrogen-ammonia gas mixture being controlled at a linear space velocity of 7 to 9 cm/second, the temperature of the reaction system was maintained at 225° C. At the same time, aniline was continuously fed from the bottom of the reaction column so as to maintain the liquid level in the column at a constant level, whereby the reaction was allowed to proceed in a steady state.

The product gas from the reaction column was cooled by a condenser to 60° C. under the above pressure, whereby it was separated into a vapor phase consisting essentially of hydrogen and ammonia gases and a liquid phase consisting essentially of the product cyclohexylamine, unreacted aniline and byproducts.

The above vapor phase was re-used as a portion of the hydrogen-ammonia gas mixture fed to the reaction column. After the reaction had reached a steady state, the liquid phase was found to be composed of 75% cyclohexylamine, 15% dicyclohexylamine, 9% unreacted aniline and N-cyclohexylaniline, and not more than 1% hydrocarbons such as cyclohexene and cyclohexane.

The above liquid phase was led to a first fractionating column with 40 bubble cap trays at atmospheric pressure, whereby a low-boiling fraction (cyclohexane, cyclohexene and other hydrocarbons) was recovered from the column top, while the bottoms were led to a second fractionating column with 45 bubble cap trays. The desired cyclohexylamine was obtained from the top of this second fractionating column, while the unreacted aniline and high-boiling byproducts (dicyclohexylamine, N-cyclohexylaniline, etc.) were recovered as distillation residues from the bottom.

The unreacted aniline and high-boiling byproducts were recycled to the reaction system. The amount of the mixture of aniline and high-boiling byproducts so recycled was 0.25 to 0.3 part by weight per part by weight of the aniline feed. The pressure and temperature of the reaction system and the feeding rate of hydrogen-ammonia gas mixture were maintained as above and the fresh raw starting material aniline, unreacted aniline and high-boiling byproducts were continuously introduced from the bottom of the reaction column so as to maintain the liquid level in the reactor at a constant level to thereby maintain the reaction in the steady state.

Then, in the same manner as mentioned above, the product gas was cooled, the vapor phase was recycled to the reaction system, the liquid phase was fractionated to separate the cyclohexylamine, and the unreacted aniline and high-boiling byproducts were returned to the reaction system. In this manner, the reaction procedure was continuously carried out.

As a result, 49.6 tons of product cyclohexylamine was produced from 50 tons of aniline feed. The purity of the cyclohexylamine thus produced was 99.9%.

EXAMPLE 2

Using N,N-dimethylaniline in lieu of aniline and using dimethylamine in place of ammonia, the hydrogenation reaction was conducted under otherwise the same conditions as in Example 1.

As a result, N,N-dimethylcyclohexylamine with a purity of 99.9% was obtained in a yield of 99.5% based on the starting material N,N-dimethylaniline.

EXAMPLE 3

Using Raney nickel catalyst in lieu of the stabilized nickel catalyst, the hydrogenation reaction was conducted under otherwise the same conditions as in Example 1. As a result, cyclohexylamine with a purity of 99.9% was produced in a yield of 99.4% based on aniline feed.

EXAMPLE 4

Using p-methylaniline in lieu of aniline and using ammonia, the hydrogenation reaction was conducted under otherwise the same conditions as in Example 1.

As a result, 4-methylcyclohexylamine with a purity of 99.8% was obtained in a yield of 99.3% based on the starting material p-methylaniline.

COMPARATIVE EXAMPLE 1

A 200 ml autoclave was charged with 35 g of aniline and 2 g of stabilized nickel catalyst and the hydrogenation reaction was conducted at a hydrogen pressure of 70 kg/cm$^2$ and a temperature of 200° C. until the hydrogen ceased to be absorbed. The reaction time was 30 minutes. This reaction yielded 34.5 g of hydrogenation product. The composition of the product was 24% cyclohexylamine, 63% aniline, 11% dicyclohexylamine, 0.3% cyclohexene and cyclohexane (each), and 1% polymer.

What is claimed is:

1. A method for continuous production of a cyclohexylamine compound by liquid phase hydrogenation of an aniline compound selected from aniline, nuclearly lower alkyl-substituted aniline, N-(lower alkyl)aniline and N,N-di(lower alkyl)aniline with hydrogen gas in the presence of a nickel catalyst, which comprises continuously feeding an aniline compound, continuously hydrogenating the aniline compound in the absence of a solvent and in the presence of an ammonia compound at a reaction pressure of about 2 to 10 kg/cm$^2$ and at about 210° to 240° C., continuously withdrawing a product gas containing product cyclohexylamine compound, unreacted aniline compound, byproducts, hydrogen and ammonia compound from the reaction system, separating the hydrogen and ammonia compound from the product gas, separating the unreacted aniline compound and byproducts from the cyclohexylamine compound and recycling the unreacted aniline compound and byproducts to the reaction system continuously together with starting material feed aniline compound, wherein the ammonia compound is ammonia when the aniline compound is aniline or nuclearly lower alkyl-substituted aniline; the ammonia compound is mono(lower alkyl)amine when the aniline compound is N-(lower alkyl)aniline; and the ammonia compound is di(lower alkyl)amine when the aniline compound is N,N-di(lower alkyl)aniline and wherein the hydrogen and ammonia compound are fed in the form of a gas mixture such that the mol ratio of hydrogen to ammonia compound is 5:0.5-3.

2. The method according to claim 1 wherein said aniline compound is aniline, nuclearly monomethyl-substituted aniline, nuclearly monoethyl-substituted aniline or nuclearly dimethyl-substituted aniline, and said ammonia compound is ammonia.

3. The method according to claim 1 wherein said aniline compound is selected from the group consisting of N-(C$_1$-C$_2$ alkyl)aniline and N,N-di(C$_1$-C$_2$ alkyl)aniline, and said ammonia compound is selected from the group consisting of mono(C$_1$-C$_2$ alkyl)amine and di(C$_1$-C$_2$ alkyl)amine, respectively.

4. The method according to claim 1 wherein hydrogen and ammonia compound are fed in the form of a gas mixture of hydrogen and ammonia compound with a mol ratio of about 5:0.5-3 at a linear space velocity of about 2 to 20 cm/second.

5. The method according to claim 4 wherein said linear space velocity is about 7 to 9 cm/second.

6. The method according to claim 1 wherein the reaction pressure is about 6.5 to 7.5 kg/cm$^2$.

7. The method according to claim 1 wherein the hydrogen and ammonia compound in the product gas are recycled to the reaction system.

8. The method according to claim 1 wherein the unreacted aniline compound and byproducts are recycled in a proportion of 0.05 to 0.5 part by weight per part by weight of feed aniline compound.

9. The method according to claim 1 wherein the feed aniline compound and recycled unreacted aniline compound and byproducts are continuously fed so that the liquid level in the reaction system can be kept at a constant level.

10. The method for continuous production of cyclohexylamine by liquid phase hydrogenation of aniline with hydrogen gas in the presence of a nickel catalyst, which comprises continuously feeding aniline, continuously hydrogenating the aniline in the absence of a solvent and in the presence of ammonia at a reaction pressure of about 2 to 10 kg/cm$^2$ and at about 210° to 240° C., continuously withdrawing a product gas containing product cyclohexylamine, unreacted aniline, byproducts, hydrogen and ammonia from the reaction system, separating the hydrogen and ammonia from the product gas, separating the unreacted aniline and byproducts from the cyclohexylamine and recycling the unreacted aniline and byproducts to the reaction system continuously together with starting material feed aniline.

* * * * *